(12) United States Patent
Ross

(10) Patent No.: US 8,505,376 B2
(45) Date of Patent: Aug. 13, 2013

(54) DOWNHOLE FLOW METER

(75) Inventor: Donald Ross, Aberdeen (GB)

(73) Assignee: Schlumberger Technology Corporation, Sugar Land, TX (US)

(*) Notice: Subject to any disclaimer, the term of this patent is extended or adjusted under 35 U.S.C. 154(b) by 461 days.

(21) Appl. No.: 12/916,158

(22) Filed: Oct. 29, 2010

(65) Prior Publication Data

US 2012/0103082 A1    May 3, 2012

(51) Int. Cl.
    *E21B 47/10*      (2012.01)
    *G01F 15/00*      (2006.01)

(52) U.S. Cl.
    USPC .................... 73/152.29; 73/861.77

(58) Field of Classification Search
    USPC .............. 73/152.29, 152.34, 152.35, 861.71, 73/861.74, 861.77, 861.78, 861.353
    See application file for complete search history.

(56) References Cited

U.S. PATENT DOCUMENTS

| | | | | |
|---|---|---|---|---|
| 2,029,633 A * | 2/1936 | Muhleisen | ................. | 73/861.75 |
| 2,868,012 A * | 1/1959 | Lebourg | .................... | 73/152.34 |
| 3,857,277 A * | 12/1974 | Moore | ...................... | 73/861.74 |
| 3,955,415 A * | 5/1976 | Sharon | ...................... | 73/861.74 |
| 4,625,565 A * | 12/1986 | Wada et al. | ................ | 73/861.74 |
| 4,840,061 A * | 6/1989 | Peltier | ......................... | 73/152.21 |
| 4,931,776 A * | 6/1990 | Klos et al. | ..................... | 340/610 |
| 5,094,103 A * | 3/1992 | Wicks et al. | ............... | 73/152.31 |
| 5,139,094 A | 8/1992 | Prevedel et al. | | |
| 5,178,006 A * | 1/1993 | Wicks et al. | ............... | 73/152.29 |
| 5,932,814 A * | 8/1999 | Hutchinson | ............... | 73/861.75 |
| 6,032,540 A * | 3/2000 | Hawkins | ..................... | 73/861.75 |
| 6,196,070 B1 * | 3/2001 | Piascik et al. | ............ | 73/861.74 |
| 6,367,336 B1 * | 4/2002 | Martina et al. | ........... | 73/861.74 |
| 6,730,927 B1 * | 5/2004 | Smith et al. | ................... | 250/573 |
| 6,769,299 B2 * | 8/2004 | Forster et al. | ............. | 73/204.26 |
| 7,007,557 B1 * | 3/2006 | Richard | ..................... | 73/861.74 |
| 7,299,819 B1 * | 11/2007 | Fenton et al. | ................ | 137/493 |
| 7,318,357 B1 * | 1/2008 | Troccoli et al. | ............ | 73/861.74 |
| 7,530,392 B2 | 5/2009 | Sugiyama et al. | | |
| 7,921,726 B2 * | 4/2011 | Ellegood | ......................... | 73/740 |
| 2006/0008913 A1 | 1/2006 | Angelescu et al. | | |
| 2007/0142547 A1 | 6/2007 | Vaidya et al. | | |
| 2008/0135239 A1 | 6/2008 | Edwards | | |

* cited by examiner

*Primary Examiner* — John Fitzgerald

(57) ABSTRACT

A technique facilitates flow monitoring in a well. A well component is designed for engagement with a well string deployed downhole into a wellbore. The well component has an internal flow passage through which well fluid is flowed. A sensor structure is mounted in the well component along the internal flow passage and comprises at least one sensor designed to sense a parameter related to fluid flow. The sensor structure is movable between a non-intrusive flow position with respect to the internal flow passage and a measurement position within the internal flow passage for measurement of the desired parameter.

24 Claims, 3 Drawing Sheets

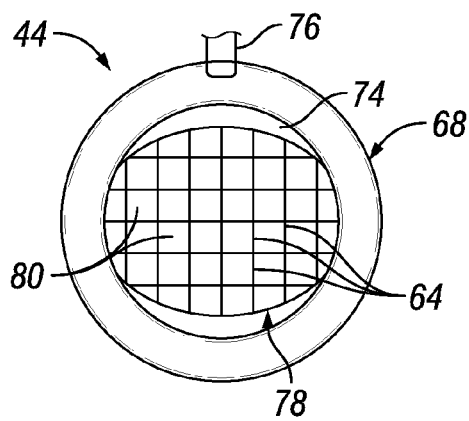
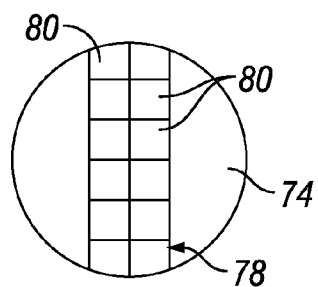
FIG. 6
FIG. 7
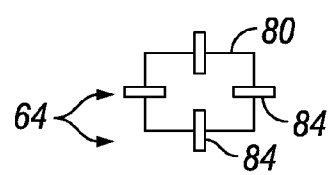
FIG. 8A
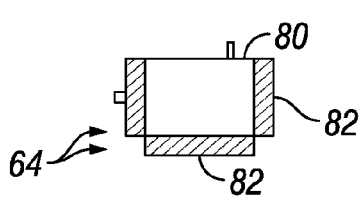
FIG. 8B
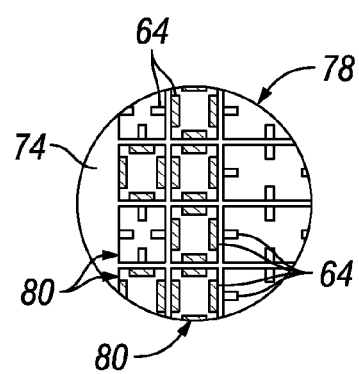
FIG. 9

DOWNHOLE FLOW METER

BACKGROUND

In many well applications, various types of flow meters and associated equipment are employed to monitor fluid flow through wellbore equipment. Some flow meters include a venturi section designed to provide a mass rate measurement as fluid passes through the venturi. The design of these types of flow meters causes a physical disruption to the flow and pressure regime to give a conditioning effect to the fluids as they pass through the venturi.

Existing flow meters present challenges in certain types of applications, e.g. clean-up applications and intervention applications, when tools are conveyed to a position below the flow meter. The venturi section may block passage of such tools and thus require several runs on coiled tubing or slick line for removal of the venturi section. Once the venturi section is removed, intervention below the flow meter may be performed for remedial or logging purposes.

In some applications, the flow meters also are limited by orientation requirements. For example, certain flow meter orientations can lead to uncertainty of measurements taken in stratified flow, e.g. flow with limited mixing of water, oil and gas. In general, venturi meters are not set in the horizontal plane due to slip iterations between the phases. In other words, gravity is used to support a venturi based flow measurement for slip correction and thus such flow meters are deployed in vertical or low deviation planes. Some flow meters also present problems during run in hole operations. For example, the flow meters may require a relatively slow run in hole process while providing potential debris gathering points along the throat of the venturi.

SUMMARY

In general, the present invention provides a technique which enables less intrusive flow monitoring in a well. The present technique utilizes a well component designed for engagement with a well string deployed downhole. The well component also has an internal flow passage through which well fluid is flowed. A sensor structure is mounted in the well component along the internal flow passage and comprises at least one sensor designed to sense a parameter related to fluid flow. The sensor structure is movable between a non-intrusive flow position with respect to the internal flow passage and a measurement position within the internal flow passage for measurement of the desired parameter.

BRIEF DESCRIPTION OF THE DRAWINGS

Certain embodiments of the invention will hereafter be described with reference to the accompanying drawings, wherein like reference numerals denote like elements, and:

FIG. 6 is an illustration of one example of a lattice sensor system design, according to an embodiment of the present invention;

FIG. 7 is an illustration of another example of a lattice sensor system design, according to an embodiment of the present invention;

FIG. 8 is an illustration of different types of small lattice units or cells of a lattice sensor system design, according to an embodiment of the present invention; and FIG. 9 is an illustration of another example of a lattice sensor system design utilizing different types of lattice sensing units, according to an embodiment of the present invention.

DETAILED DESCRIPTION

In the following description, numerous details are set forth to provide an understanding of the present invention. However, it will be understood by those of ordinary skill in the art that the present invention may be practiced without these details and that numerous variations or modifications from the described embodiments may be possible.

The present invention generally relates to a system and method for monitoring flow in a well. The technique employees a well component, such as a gauge mandrel, coupled into a well string and deployed in a wellbore. A main fluid flow passage is oriented generally longitudinally through the well component to accommodate fluid flow, e.g. production fluid flow, through the well string. A sensor structure is mounted in the well component and comprises at least one sensor for monitoring one or more flow related parameters as fluid flows along the main fluid flow passage. The sensor structure is coupled with an actuator which may be selectively operated to move the sensor structure into and out of the flow of fluid moving through the well component.

Because the sensor structure may be selectively moved to a non-intrusive position out of the fluid flow region, the present system and methodology facilitates running in hole operations, such as intervention operations. In certain embodiments, the sensor structure may be fully removed from the flow path to expose a full bore flow area along the main fluid flow passage. The technique also reduces the conditioning of the fluid and thus can be used to provide a cross correlation type measurement as opposed to physical measurements, at least in some embodiments.

In one specific example, the sensor structure comprises a lattice flow meter structure which can be used in any orientation plane, including the horizontal plane. This type of sensor structure is useful in measuring parameters in a variety of flow regimes, including tri-phase stratified flow regimes. Initially, the well string/completion is run with the sensor structure located at a non-invasive position to allow flow without accumulation of debris. When operations to run the completion are finalized, a signal is sent downhole to an actuator which moves the sensor structure into the flow region. With the lattice flow meter structure, for example, the signal causes one or more lattice meter arms to move curved lattice measurement subs into the flow path. By way of example, a single lattice sub may be used for flow measurements in various applications. In other embodiments, a second lattice sub may be employed for cross correlation purposes and/or redundancy. In this example, the system enables full bore flow for certain operations and also accurate measurement of flow parameters when desired.

Figure 1:
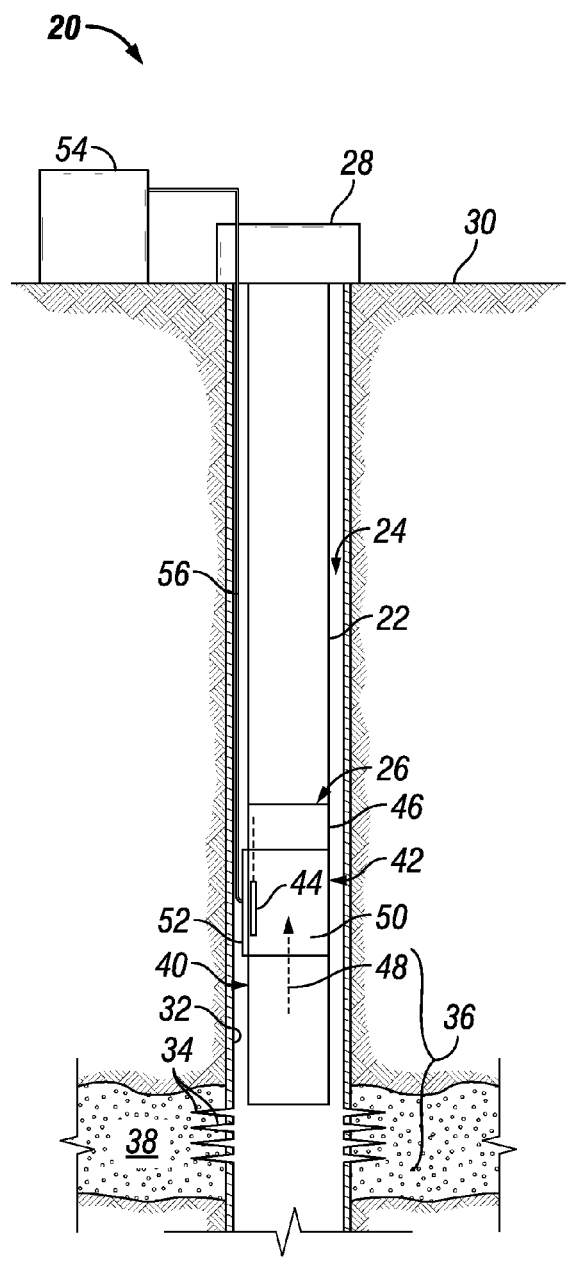
FIG. 1 is an illustration of a well string having one embodiment of a flow meter system deployed in a wellbore, according to an embodiment of the present invention.

Referring generally to FIG. 1, an embodiment of a well system 20 is illustrated as having a well string 22 deployed in a wellbore 24. The well string 22 may comprise a completion 26 positioned at a desired downhole location within wellbore 24. As illustrated, the well string 22 extends downwardly from surface equipment 28, such as a wellhead, positioned at a surface location 30. In some applications, wellbore 24 is lined with a liner or casing 32. A plurality of perforations 34 may be formed through the casing 32 to enable inflow (or outflow) of fluid with respect to a well zone 36 of a surrounding formation 38.

Completion 26 may be constructed in a variety of configurations with many types of components 40 depending on the specific well application. Additionally, the system and methodology described herein for monitoring parameters related to flow in a wellbore may be combined with many other components and downhole well equipment configurations. In the embodiment illustrated, completion 26 comprises a sensor assembly 42 having a sensor structure 44 and an actuator 46 coupled to the sensor structure 44. The actuator 46 is operated to move the sensor structure 44 into and out of a flow region, which is represented by the arrow labeled 48.

In the embodiment illustrated, sensor structure 44 is mounted in a gauge mandrel 50 having an eccentric portion 52 which facilitates movement of the sensor structure 44 out of flow region 48. Gauge mandrel 50 may be formed as a full bore tubing joint in some applications. The actuator 46 and sensor structure 44 may be coupled to one or more corresponding control systems 54 via one or more communication lines 56. By way of example, control system 54 may be a single control system located at surface 30 (or another suitable location) and connected with actuator 46 and sensor structure 44 by a plurality of communication lines 56.

Communication lines 56 may have a variety of forms depending on the type of actuator 46. For example, communication lines 56 may comprise electrical and/or optical fiber data lines for carrying sensor data uphole to control system 54 for processing. The communication lines 56 also may comprise electrical and/or hydraulic communication lines for controlling actuator 46. Actuator 46, in turn, may comprise a movable sleeve or other type of hydraulic actuator which receives hydraulic fluid through the corresponding communication line 56.

In one specific example, actuator 46 is a hydraulic system having a hydraulic piston selectively moved via hydraulic fluid which may be activated by an electrohydraulic pump. In other embodiments, however, actuator 46 may comprise a variety of electric actuators, e.g. solenoids, which are selectively operated to move sensor structure 44 between desired positions. By way of another example, the actuator 46 may comprise an electric motor coupled to a screw and ball system to selectively move the sensor structure 44 between desired positions, e.g. in and out of the fluid flow stream. The type of actuator 46 and the mechanisms for coupling actuator 46 with sensor structure 44 vary according to the applications in which sensor assembly 42 is employed to monitor desired flow related parameters.

Figure 2:
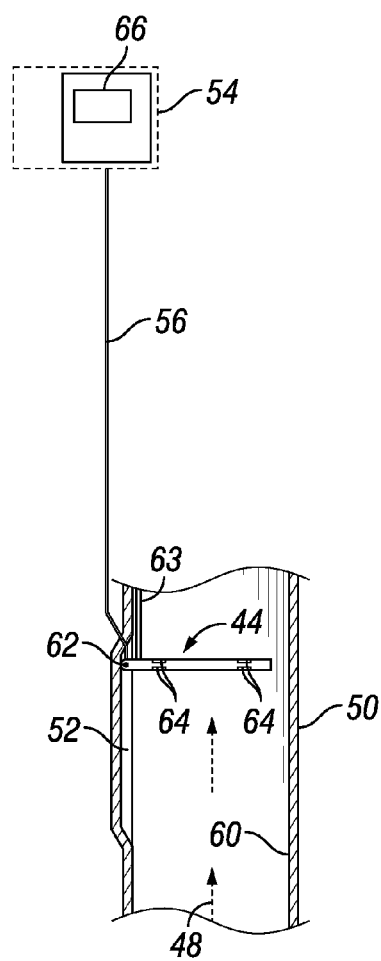
FIG. 2 is a schematic illustration of examples of sensors which may be utilized in the flow meter system, according to an embodiment of the present invention.

In the embodiment illustrated in FIG. 2, sensor structure 44 is pivotably mounted in gauge mandrel 50 and is selectively pivotable into and out of fluid flow along flow region 48 which is defined by an interior 60 of the gauge mandrel 50. As illustrated, the sensor structure 44 may be mounted to the gauge mandrel 50 by a pivot 62 which allows pivotable movement under the direction of an actuator mechanism 63, e.g. a sleeve, link, or other appropriate mechanism, of actuator 46. In this particular example, the sensor structure 44 may be pivoted completely into eccentric portion 52 to enable full bore flow along the interior 60 of gauge mandrel 50 and well string 22.

As further illustrated in FIG. 2, sensor structure 44 may comprise one or more sensors 64. In the particular example illustrated, the movable sensor structure 44 comprises a plurality of sensors 64 which are designed to detect and monitor a variety of parameters related to fluid flow along the well string 22. In some applications, the plurality of sensors 64 provides integrated measurements of a plurality of flow related parameters. In one example, sensors 64 measure the time of passage as fluid flows through the sensor structure. Sensor 64 also may comprise sensors designed to measure temperature, pressure, capacitance, density, volume of flow, mass flow rate, and other parameters related to the flow of fluid. In one specific embodiment, the sensor structure 44 is a lattice sensor structure comprising a lattice sub mounted in gauge mandrel 50, as described in greater detail below.

Data from the one or more sensors 64 may be processed to determine desired attributes of the flowing fluid. By way of example, the data is processed on a processor-based system 66 which may be part of the larger overall control system 54. Data based on individual parameters monitored, or on various combinations of parameters monitored, may be processed according to desired models, algorithms, or other tools to obtain the desired understanding of fluid flow along well string 22. However, during run in or at other times when sensor data is not required, sensor structure 44 may simply be moved to a non-intrusive position relative to fluid flow along well string 22.

Figure 3:
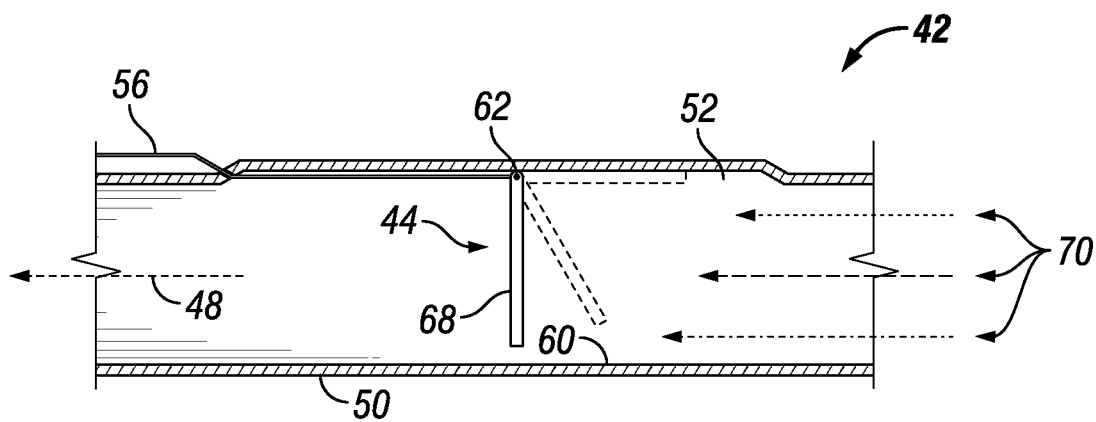
FIG. 3 is an illustration of one example of the flow meter system, according to an embodiment of the present invention.

Referring generally to FIG. 3, an embodiment is illustrated in which movable sensor structure 44 comprises an individual lattice sensor structure in the form of a lattice flow sub 68. The lattice flow sub 68 is pivotably mounted in eccentric portion 52 of gauge mandrel 50 and may be actuated via actuator 46, e.g. a hydraulic actuator, after the well has been completed successfully and has been placed into production. As illustrated, the lattice flow sub 68 is moved, e.g. pivoted, into the flow region 48 to detect parameters of flowing fluid 70 which may comprise constituents, such as oil, gas and water. The sensors 64 are encased in the lattice flow sub 68 and may include a plurality of pressure sensors, temperature sensors, density sensors, resistance sensors, capacitance sensors, and other types of sensors each covering its own portion of a flow area. Additionally, the one or more sensors 64 may comprise a flow spinner designed to detect the various fluid flows of a stratified flowing fluid 70.

Figure 4:
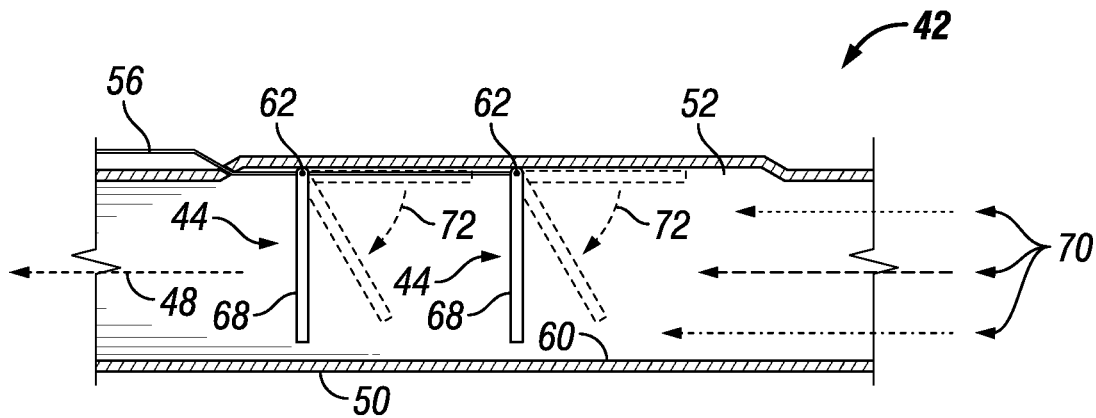
FIG. 4 is an illustration of another example of the flow meter system, according to an alternate embodiment of the present invention.

In FIG. 4, another embodiment of sensor assembly 42 is illustrated as having a pair of movable sensor structures 44. The sensor structures 44 may be positioned in sequence within gauge mandrel 50 for selective movement between a non-invasive position and a position in the flow region 48, as illustrated. By way of example, the sequential sensor structures 44 may comprise lattice sensor structures in the form of sequential lattice flow subs 68 which are movably, e.g. pivotably, mounted in eccentric portion 52 of gauge mandrel 50. The lattice flow subs 68 may be actuated individually or collectively via an appropriate actuator or actuators 46.

According to one operational example, the well string 22 is run in hole with the pair of lattice flow subs 68 located at a non-invasive position within eccentric portion 52 of the gauge mandrel/tubing joint. Once on depth and with the well flowing, the pair of lattice flow subs is actuated into the flow path, as represented by arrows 72. Each lattice flow sub 68 may again contain encased sensors 64, e.g. pressure sensors, temperature sensors, density sensors, resistance sensors, capacitance sensors, flow spinners, and other types of sensors, each covering a portion of the flow area.

Figure 5:
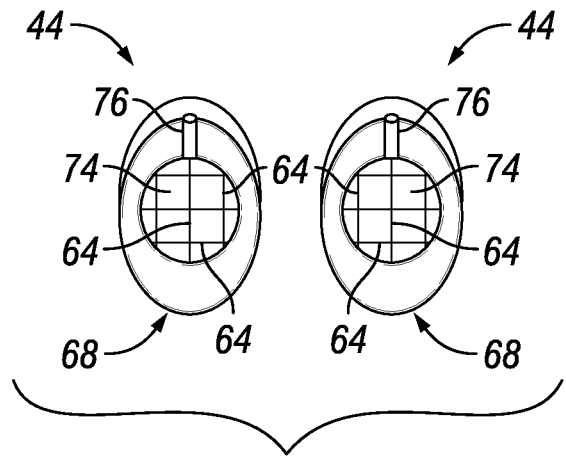
FIG. 5 is an illustration of one example of a movable sensor structure employed in the flow meter system, according to an embodiment of the present invention.

As further illustrated in FIG. 5, each lattice flow sub 68 comprises a lattice flow area 74 which may be in the form of a central longitudinal opening through a sub having a generally circular configuration. The lattice flow area 74 may be designed to allow flow through a plurality of lattice units carrying sensors 64. By using a pair of the lattice flow subs 68, as illustrated in FIGS. 4 and 5, the combination allows acquisition of additional integrated measurements, such as time of flight measurements between sequential lattice flow subs 68. However, the second movable sensor structure 44, e.g. lattice flow sub 68, may simply be used for cross correlation purposes and/or redundancy.

Lattice flow subs 68 may be connected to the gauge mandrel 50 by a variety of mechanisms which allow movement of each lattice flow sub. By way of example, each lattice flow sub 68 may be coupled with pivot 62 via an appropriate arm 76 which allows pivoting motion of the lattice flow sub 68 between the non-invasive position and the in-flow position.

Referring generally to FIG. 6, one example of a lattice sensor design 78 is illustrated as having a plurality of lattice sensor units 80 which may be positioned through lattice flow area 74 of each lattice sub 68. The number, type and configuration of lattice sensor units 80 depends on the number and type of sensors 64 to be incorporated into a given lattice sub 68. In the embodiment illustrated in FIG. 6, the lattice sensor units 80 are formed by various cross members carrying sensors designed to detect and monitor a plurality of desired fluid flow related parameters. The lattice sensor units may be placed in various configurations to determine, for example, flow regime and/or fluid properties in a stratified flowing well.

In FIG. 6, numerous lattice units 80 are illustrated has spread throughout lattice flow area 74 to determine multiple parameters, such as fluid type, fluid rate, fluid properties, and current flow regime. However, other configurations of the lattice sensor design 78 may be selected to obtain a more limited set of measurements. In the embodiment illustrated in FIG. 7, for example, a reduced group of lattice sensor units 80 is employed to detect and monitor a more limited number of fluid flow parameters, e.g. fluid properties only.

Individual lattice sensor units 80 are illustrated in FIG. 8 as examples of a wide variety of lattice sensor units 80 which may employ many types of sensors 64 to detect desired parameters of fluid flowing through the lattice flow area 74. For example, the sensor units 80 may comprise a variety of membranes 82, electrodes 84, and other types of sensors incorporated into the sensor units 80 to detect the desired flow related parameters. Electrodes also may be used to form connections between the lattice units 80.

Lattice units 80 and sensors 64 may be combined in numerous configurations to achieve the detection and monitoring of parameters for a given application. In FIG. 9, for example, an embodiment of the lattice sensor design 78 is illustrated in which various lattice units 80, such as those illustrated in FIG. 8, have been combined in specific groupings within a single lattice flow area 74 to measure a wide variety of flow related parameters. By way of example, the leftmost column of sensor units 80 in FIG. 9 is a group of sensor units configured to provide dielectric and capacitance monitoring. The center column of sensor units 80 comprises sensors 64, e.g. membranes, designed to provide chemical sensing capability. The rightmost column comprises a group of sensor units 80 which cooperate to monitor fluid flow and flow regime parameters. Furthermore, electrodes may be employed to provide connections between some or all of the sensor units 80 to facilitate transmission of sensor data through the lattice sub 68 to the appropriate communication line 56 for transfer to processor 66. As discussed above, additional lattice subs 68 also may be employed to provide additional measurements and/or correlation and redundancy measurements.

Depending on the specifics of the application and the wellbore environment, the movable sensor structure 44 may be mounted in a variety of completion components or other downhole components. The number of movable sensor structures 44 also can be adapted to the specific requirements of a given application. Similarly, the type of actuator may vary depending on various factors, such as environment, type of completion, configuration of the sensor structure, and the desired sensor structure movement. For example, although the sensor structure may be pivoted into and out of the fluid flow, other types of motion also may be used to transition the sensors between a non-invasive position and a position in the flow of fluid. Additionally, the embodiments described herein enable monitoring of desired flow related parameters in many types of wells, including vertical wells and substantially deviated, e.g. horizontal, wells.

Although only a few embodiments of the present invention have been described in detail above, those of ordinary skill in the art will readily appreciate that many modifications are possible without materially departing from the teachings of this invention. Accordingly, such modifications are intended to be included within the scope of this invention as defined in the claims.

What is claimed is:

1. A system for monitoring flow, comprising:
a well string having: a gauge mandrel with an eccentric portion; and a lattice sensor structure pivotably mounted in the eccentric portion, the lattice sensor structure comprising at least one sensor to obtain flow related measurements, wherein the lattice sensor structure is selectively pivotable into and out of a fluid flow through the well string.

2. The system as recited in claim 1, wherein the well string further comprises a second lattice sensor structure pivotably mounted in the eccentric portion.

3. The system as recited in claim 1, wherein the gauge mandrel is formed as a full bore tubing joint.

4. The system as recited in claim 1, wherein the well string further comprises an instrument line extending from the lattice sensor structure to a surface location.

5. The system as recited in claim 1, wherein the lattice sensor structure comprises a plurality of sensors to provide integrated measurements of flow related parameters.

6. The system as recited in claim 5, wherein the plurality of sensors measures time of passage as fluid flows through the lattice sensor structure.

7. The system as recited in claim 5, wherein the plurality of sensors measures temperature.

8. The system as recited in claim 5, wherein the plurality of sensors measures pressure.

9. The system as recited in claim 5, wherein the plurality of sensors measures capacitance.

10. The system as recited in claim 5, wherein the plurality of sensors measures density.

11. A method of monitoring flow in a wellbore, comprising:
pivotably mounting a flow monitoring sensor structure within a gauge mandrel having a production fluid flow passage extending longitudinally through the gauge mandrel;

delivering the gauge mandrel downhole into a wellbore with the flow monitoring sensor structure located in a non-intrusive position with respect to the production fluid flow passage; and at a desire downhole location, pivoting the flow monitoring sensor structure into the production fluid flow passage.

12. The method as recited in claim 11, wherein pivoting comprises utilizing a hydraulic actuator to pivot the flow monitoring sensor structure between the position in the production fluid flow passage and the non-intrusive position.

13. The method as recited in claim 11, further comprising monitoring fluid flow along the fluid flow passage.

14. The method as recited in claim 13, wherein monitoring comprises monitoring a flow rate.

15. The method as recited in claim 13, wherein monitoring comprises monitoring a pressure.

16. The method as recited in claim 13, wherein monitoring comprises monitoring a temperature.

17. The method as recited in claim 13, wherein monitoring comprises monitoring a capacitance.

18. The method as recited in claim 13, wherein monitoring comprises monitoring a density.

19. A system for monitoring parameters related to flow in a wellbore, comprising:

a well component having an internal flow passage;

a sensor structure mounted in the well component, the sensor structure having at least one sensor for monitoring a flow related parameter; and an actuator mechanism coupled to the sensor structure, the actuator mechanism being controllable to selectively move the sensor structure into and out of the internal flow passage.

20. The system as recited in claim 19, wherein the sensor structure comprises a pair of sequential sensor structures.

21. The system as recited in claim 19, wherein the sensor structure is generally circular with a central flow opening.

22. The system as recited in claim 21, wherein the at least one sensor comprises a plurality of sensors exposed to fluid flow through the central flow opening.

23. The system as recited in claim 19, wherein the sensor structure is pivotably mounted to the well component.

24. The system as recited in claim 23, wherein the well component comprises a gauge mandrel with an eccentric portion in which the sensor structure is pivotably mounted.

* * * * *